US006242646B1

(12) United States Patent
Sistig et al.

(10) Patent No.: US 6,242,646 B1
(45) Date of Patent: Jun. 5, 2001

(54) METHOD OF PRODUCING 2,4-DICHLORO-5-HYDROXYACETANILIDE

(75) Inventors: Frank Sistig, Idstein; Hans-Jürgen Leitung; Stefan Krause, both of Frankfurt am Main, all of (DE)

(73) Assignee: Clariant GmbH, Frankfurt am Main (DE)

( * ) Notice: Subject to any disclaimer, the term of this patent is extended or adjusted under 35 U.S.C. 154(b) by 0 days.

(21) Appl. No.: 09/647,305
(22) PCT Filed: Mar. 25, 1999
(86) PCT No.: PCT/EP99/02017
§ 371 Date: Sep. 27, 2000
§ 102(e) Date: Sep. 27, 2000
(87) PCT Pub. No.: WO99/50228
PCT Pub. Date: Oct. 7, 1999

(30) Foreign Application Priority Data

Mar. 27, 1998 (DE) .............................. 198 13 886

(51) Int. Cl.⁷ .................................. C07C 235/00
(52) U.S. Cl. ............................................. 564/223
(58) Field of Search ................................. 564/223

(56) References Cited

FOREIGN PATENT DOCUMENTS

WO 85/01939    5/1985  (WO) .
WO 86/00072    1/1986  (WO) .

OTHER PUBLICATIONS

Patent Abstract for JP 61 044856, 4/1986.
Patent Abstract for JP 61 047450 3/1986.
W. A. Jacobs et al., Journal of the American Chemical Society, Bd, 41, 1919, pp. 458–474, "On certain aromatic amines and chloroacetyl derivatives."

*Primary Examiner*—Samuel Barts
(74) *Attorney, Agent, or Firm*—Scott E. Hanf

(57) ABSTRACT

The present invention relates to a process for preparing 2,4-dichloro-5-hydroxyacetanilide by reacting 3-hydroxyacetanilide with sulfuryl chloride in the presence of from 3 to 30 parts by weight of an aliphatic carboxylic acid having from 1 to 6 carbon atoms per part by weight of 3-hydroxyacetanilide with vigorous mixing at from 20 to 100°, removing gaseous components from the reaction mixture, setting a ratio of from 1.0 to 6 parts by weight of aliphatic carboxylic acid per part by weight of 3-hydroxyacetanilide employed and removing 2,4-dichloro-5-hydroxyacetanilide as a solid.

10 Claims, No Drawings

METHOD OF PRODUCING 2,4-DICHLORO-5-HYDROXYACETANILIDE

CROSS REFERENCES TO RELATED APPLICATIONS

This application is a 371 of PCT/EP99/02017 filed Mar. 25, 1999.

The present invention is described in the German priority application No. DE 198 13 886.5, filed Mar. 27, 1998, which is hereby incorporated by reference as is fully disclosed herein.

BACKGROUND OF THE INVENTION

The present invention relates to a process for preparing 2,4-dichloro-5-hydroxyacetanilide, said process being an advance on the prior art.

2,4-Dichloro-5-hydroxyacetanilide is an important intermediate in the preparation of crop protection agents (WO 85/01939).

2,4-Dichloro-5-hydroxyacetanilide can be prepared by chlorination of 3-hydroxyacetanilide, which is obtainable by acetylation of 3-aminophenol.

The reaction of 3-hydroxyacetanilide with gaseous chlorine in glacial acetic acid described in WO 86/00072 on page 25 under Example III Step B leads to a yield of only 30.4% of theory, based on 3-hydroxyacetanilide employed.

With reference to Example 2 Step B, WO 85/01939 describes, on page 27 under Example 3 Step B, the reaction of 3-hydroxyacetanilide with sulfuryl chloride in glacial acetic acid. According to the specifications on page 25 Example 2 Step B, in the preparation of 2,4-dichloro-5-methylacetanilide, the reaction mixture is, after the addition of sulfuryl chloride to 3-acetamidotoluene, allowed to stand at room temperature for approximately 60 hours and subsequently heated, until a stirrable material is formed, and then stirred for approximately 5 hours more. The 2,4-dichloro-5-hydroxyacetanilide prepared in accordance with Example 3 Step B in a similar manner to Example 2 Step B is obtained in a yield of 43.5%, based on 3-hydroxyacetanilide employed.

The yields of 2,4-dicholor-5-hydroxyacetanilide obtained in the two examples described above are comparatively low, and the processes are therefore not to be recommended for industrial realization.

SUMMARY OF THE INVENTION

It was therefore the object to develop a process which on the one hand can be realized industrially in a simple manner and which additionally makes available, at reasonable cost, 2,4-dicholor-5-hydroxyacetanilide, in high yields and at the same time in high purity.

DESCRIPTION OF THE PREFERRED EMBODIMENT

This object is achieved by a process for preparing 2,4-dichloro-5-hydroxyacetanilide by reacting 3-hydroxyacetanilide with sulfuryl chloride in the presence of from 3 to 30 parts by weight of an aliphatic carboxylic acid having from 1 to 6 carbon atoms per part by weight of 3-hydroxyacetanilide with vigorous mixing at from 20 to 100° C., removing gaseous components from the reaction mixture, setting a ratio of from 1.0 to 6 parts by weight of aliphatic carboxylic acid per part by weight of 3-hydroxyacetanilide employed and removing 2,4-dichloro-5-hydroxyacetanilide as a solid.

With a view to the preparation of 2,4-dichloro-5-hydroxyacetanilide described in WO 85/01939 under Example 3 Step B, it is very surprising that the process according to the invention affords the desired 2,4-dicholor-5-hydroxyacetanilide in a yield of from 80 to 85% and more, based on the 3-aminophenol required for preparing 3-hydroxyacetanilide. The process can be realized without any particular technical expense even at relatively low temperatures and short reaction times. The acetic acid which is separated off during the operation according to the invention can be recycled as solvent/suspending medium into the reaction.

In general, from 1.5 to 5, in particular from 1.8 to 2.5, preferably from 1.9 to 2.2, mol of sulfuryl chloride are employed per mole of 3-hydroxyacetanilide.

Based on 3-hydroxyacetanilide, the aliphatic carboxylic acid is added in such an amount that sufficient mixing of the reaction mixture is ensured during the reaction.

In a large number of cases this is ensured by carrying out the reaction of 3-hydroxyacetanilide with sulfuryl chloride in the presence of from 4 to 15, in particular from 4.5 to 13, preferably from 5 to 10, particularly preferably from 5 to 7, parts by weight of aliphatic carboxylic acid per part by weight of 3-hydroxyacetanilide.

Suitable aliphatic carboxylic acids are formic acid, acetic acid, propionic acid, n-butyric acid, isobutyric acid, 3-methylbutyric acid, valeric acid, n-hexanoic and isohexanoic acid. It is also possible to employ mixtures of the abovementioned carboxylic acids. The aliphatic carboxylic acids or their mixtures are employed in anhydrous form.

Particularly suitable aliphatic carboxylic acids are formic acid, acetic acid, propionic acid, n-butyric acid, isobutyric acid or mixtures of these carboxylic acids, in particular formic acid, acetic acid or propionic acid, preferably acetic acid.

In a large number of cases it was found to be advantageous to react 3-hydroxyacetanilide with sulfuryl chloride at from 25 to 70, in particular from 40 to 60 ° C.

The process can be carried out in a particularly simple manner by initially charging the 3-hydroxyacetanilide and the aliphatic carboxylic acid, and adding the sulfuryl chloride while mixing. The rate of addition of the sulfuryl chloride is chosen such that the heat of reaction and the gaseous components which are formed ($SO_2$, HCl) can be drawn off. The reaction time depends essentially on the rate of addition of the sulfuryl chloride and the practicability of being able to draw off both the heat of reaction and the gaseous components (waste gases) at a sufficient rate.

During the reaction, it has to be ensured that gaseous components can escape from the reaction mixture. After the addition of sulfuryl chloride has ended, the mixture is allowed to react for a sufficient extra time to bring the reaction to completion and to remove any gaseous components which may still be present.

During the reaction, it has to be ensured that the reactants are thoroughly mixed. Efficient mixing also facilitates the required removal of gaseous components from the reaction mixture during the reaction and the extra reaction time.

The gaseous components which are still dissolved after the reaction with sulfuryl chloride, for example HCl and $SO_2$, are usually removed at a pressure of from 10 mbar to atmospheric pressure, in particular from 20 mbar to 500 mbar, preferably from 50 to 250 mbar. It has to be ensured that the gaseous components are as substantially separated off from the reaction mixture as possible. Insufficient removal of the gaseous components from the reaction mixture can have disadvantageous consequences both for the yield and the purity of the end product.

In many cases, it was found to be advantageous to remove gaseous components at from 25 to 100° C., in particular from 40 to 70° C.

When separating off the gaseous components, temperature and pressure are usually chosen such that the gaseous components are removed, but not the aliphatic carboxylic acid. Thus, it is ensured that, when the aliphatic carboxylic acid is separated off by distillation, an aliphatic carboxylic acid obtained is not contaminated by HCl and $SO_2$.

As already mentioned, the ratio of aliphatic carboxylic acid to 3-hydroxyacetanilide employed is set to from 1.0 to 6, in particular from 1.5 to 5, preferably from 1.5 to 4.5, particularly preferably from 2 to 4, parts by weight of aliphatic carboxylic acid per part by weight of 3-hydroxyacetanilide employed by separating off, if required, the aliphatic carboxylic acid from the reaction mixture until the abovementioned ratio is obtained, or, if required, adding an appropriate amount of aliphatic carboxylic acid. It may not be necessary to adjust this ratio separately if, in the reaction of 3-hydroxyacetanilide with sulfuryl chloride, a ratio of aliphatic carboxylic acid to 3-hydroxyacetanilide employed which is suitable for separating off 2,4-dichloro-5-hydroxyacetanilide is set at the beginning.

The ratio of aliphatic carboxylic acid to 3-hydroxyacetanilide employed should be such that, on the one hand, the 2,4-dicholor-5-hydroxyacetanilide precipitates out as a solid as completely as possible and that, on the other hand, the reaction mixture which is obtained has sufficient flowability for further work-up (filtration, centrifugation).

In a large number of cases it was found advantageous to distill off the aliphatic carboxylic acid at from 30 to 80° C. and from 25 to 270 mbar. The reaction mixture is subsequently cooled to from 15 to 45° C., and the 2,4-dichloro-5-hydroxyacetanilide is separated off as a solid, for example by filtration.

The resulting mother liquor, which contains 2,4-dichloro-5-hydroxyacetanilide, can be recycled very successfully into the next reaction with sulfuryl chloride in an amount of from 10 to 90%, in particular from 30 to 60%, to increase the yield. The amounts of fresh aliphatic carboxylic acid employed can then be reduced correspondingly.

After washing with acetic acid and water, the 2,4-dicholor-5-hydroxyacetanilide which has been separated off as a solid is generally obtained in a purity of 98.5% and more.

Both 3-hydroxyacetanilide in isolated form or else in the form of a crude product can be employed for the process according to the invention.

According to a particular embodiment of the process according to the invention, the 3-hydroxyacetanilide used is a 3-hydroxyacetanilide-containing reaction mixture prepared by reaction of 3-aminophenol with acetic anhydride in acetic acid. This variant is particularly advantageous since this reaction mixture can be employed directly for the process without any additional purification.

For preparing this 3-hydroxyacetanilide-containing reaction mixture, 3-aminophenol is reacted in acetic acid as solvent with from 0.9 to 2, in particular from 1 to 1.2, mole of acetic anhydride. Here, it has been found to be advantageous to initially charge 3-aminophenol dissolved in acetic acid, and to add acetic anhydride slowly. The reaction is carried out at a temperature of from 0 to 120° C., in particular from 20 to 60° C. The amount of acetic acid is chosen such that the reaction partners are present in dissolved form at the reaction temperature. In many cases, from 1 to 20, in particular from 2 to 5, parts by weight of acetic acid, based on part by weight of 3-aminophenol, have been found advantageous. The reaction time results from the selected reaction temperature and the rate at which the reaction partners are added. In many cases, a reaction time of from 30 minutes to 10 hours, in particular from 1 to 3 hours, is sufficient.

After the reaction has ended, 3-hydroxyacetanilide can be crystallized out from the reaction mixture and filtered off. The crystallization is generally carried out from 0 to 40° C., in particular from 15 to 20° C.

As mentioned above, both the 3-hydroxyacetanilide in isolated form and the 3-hydroxyacetanilide-containing reaction mixture can be used for the chlorination with sulfuryl chloride without any further purification.

If such a reaction mixture is employed, it is recommended to set the required weight ratio of aliphatic carboxylic acid or acetic acid to 3-hydroxyacetanilide either by adding the aliphatic carboxylic acid, in particular acetic acid, or by removing acetic acid. By employing acetic acid as aliphatic carboxylic acid, it is possible to carry out this process variant in a particularly favorable form.

The process according to the invention can be carried out both batchwise and continuously.

The examples below illustrate the invention in more detail, without limiting it.

Experimental Part

EXAMPLES

A) Preparation of a 3-hydroxyacetanilide-containing reaction mixture

At 20° C., 262 g (2.4 mol) of 3-aminophenol are dissolved in 806 g of acetic acid. Over a period of 45 minutes, 254 g of acetic anhydride are subsequently added. After the addition has ended, the mixture is stirred at 55° C. for 5 minutes. As demonstrated by HPLC analysis, the 3-aminophenol has been converted completely into 3-hydroxyacetanilide.

The reaction mixture is used directly and without any further purification for the subsequent chlorination.

B) Preparation of 2,4-dicholor-5-hydroxyacetanilide

Example 1

Reaction of 3-hydroxyacetanilide with sulfuryl chloride
175 g (1.16 mol) of 3-hydroxyacetanilide are dissolved in 2700 g of glacial acetic acid. With vigorous stirring, 327 g (2.42 mol) of sulfuryl chloride are added dropwise at 60° C. over a period of 2 hours. After the addition has ended, the mixture is stirred at 60° C. for 5 minutes. Subsequently, at a bottom temperature of 60° C. and approximately 120 mbar, first any gases which are still dissolved are removed, and then 2000 g of acetic acid are distilled off. The suspension is cooled to 15° C., filtered off, and the residue is washed with 250 g of vinegar and 250 g of water. The filter cake is dried at approximately 200 mbar and 60° C. This gives 193 g of 2,4-dicholor-5-hydroxyacetanilide, which corresponds to a yield of 76%.

The purity of the 2,4-dicholor-5-hydroxyacetanilide—determined by HPLC—is greater than 99%.

Example 2

Reaction of 3-hydroxyacetanilide with sulfuryl chloride with recycling of the mother liquor from Example 1

175 g (1.16 mol) of 3-hydroxyacetanilide are admixed with 2430 g of glacial acetic acid and 270 g of the combined amount of mother liquor and washed vinegar originating from Example 1. With vigorous stirring, 327 g of sulfuryl chloride are added dropwise at 60° C. over a period of 2 hours. After the addition has ended, the mixture is stirred at 60° C. for 5 minutes. Subsequently, at a bottom temperature of 60° C. and approximately 120 mbar, initially still dissolved gases are removed, and then 2000 g of acetic acid are distilled off.

The suspension is stirred whilst being cooled to 15° C. and then filtered off, and the residue is washed with 250 g of acetic acid and 250 g of water. The filter cake is dried at approximately 200 mbar and 60° C. This gives 215 g of 2,4-dicholor-5-hydroxyacetanilide, which corresponds to a yield of 84%.

The purity, determined by HPLC analysis, is greater than 99%.

Example 3

Reaction of the reaction mixture prepared according to A) with sulfuryl chloride The reaction mixture prepared according to A) is admixed with 2000 g of acetic acid. Subsequently, at 30° C., 665 g of sulfuryl chloride are added dropwise with vigorous stirring over a period of 60 minutes. After the addition sulfuryl chloride has ended, the mixture is stirred at 30° C. for 5minutes. Then, at a bottom temperature of approximately 50° C. and a reduced pressure of approximately 100 mbar, first any gases which are still dissolved are removed, and then 1500 g of acetic acid are distilled off. The resulting suspension is cooled to 20° C. and filtered. The resulting filter cake is washed with 500 g of acetic acid and 500 ml of water and dried at approximately 200 mbar and 60° C.

425 g of 2,4-dicholor-5-hydroxyacetanilide, corresponding to a yield of 80%, based on 3-aminophenol, are obtained as a white solid.

The purity, determined by HPLC analysis is greater than 99%.

Example 4

Reaction of 3-hydroxyacetanilide with sulfuryl chloride in formic acid 151 g of 3-hydroxyacetanilide are dissolved in 1500 g of formic acid. At 60° C., 277 g of sulfuryl chloride are added dropwise with vigorous stirring over a period of 2 hours. After the addition has ended, the mixture is stirred at 60° C. for 5 minutes. Subsequently, at a bottom temperature of 60° C. and approximately 140 mbar, first any gases which are still dissolved are removed, and then 1050 g of formic acid are distilled off.

The suspension is stirred while being cooled to 15° C. and is then filtered off, and the residue is washed with 200 g of formic acid and 200 g of water. The filter cake is dried at approximately 200 mbar and 60° C. This gives 154 g of 2,4-dichloro-5-hydroxyacetanilide, which corresponds to a yield of 70%.

The purity, determined by HPLC analysis, is greater than 99%.

Example 5

Reaction of 3-hydroxyacetanilide with sulfuryl chloride in propionic acid

The operation is carried out as described in Example 4, with the difference that propionic acid is employed instead of formic acid.

This gives 176 g of 2,4-dicholor-5-hydroxyacetanilide, which corresponds to a yield of 80%.

The purity, determined by HPLC analysis, is greater than 99%.

What is claimed is:

1. A process for preparing 2,4-dichloro-5-hydroxyacetanilide by reacting 3-hydroxyacetanilide with sulfuryl chloride in the presence of from 3 to 30 parts by weight of an aliphatic carboxylic acid having from 1 to 6 carbon atoms per part by weight of 3-hydroxyacetanilide with vigorous mixing at from 20 to 100° C., removing gaseous components from the reaction mixture, setting a ratio of from 1.0 to 6 parts by weight of aliphatic carboxylic acid per part by weight of 3-hydroxyacetanilide employed and removing 2,4-dichloro-5-hydroxyacetanilide as a solid.

2. The process as claimed in claim 1, wherein from 1.5 to 5 mol of sulfuryl chloride are employed per mole of 3-hydroxyacetanilide.

3. The process as claimed in claim 1, wherein from 1.8 to 2.5 mol of sulfuryl chloride are employed per mole of 3-hydroxyacetanilide.

4. The process as claimed in claim 1, wherein the reaction is carried out in the presence of from 4 to 15 parts by weight of aliphatic carboxylic acid.

5. The process as claimed in claim 1, wherein the aliphatic carboxylic acid used is formic acid, acetic acid or propionic acid.

6. The process as claimed in claim 1, wherein the aliphatic carboxylic acid used is acetic acid.

7. The process as claimed in claim 1, wherein 3-hydroxyacetanilide is reacted with sulfuryl chloride at from 25 to 60° C.

8. The process as claimed in claim 1, wherein the gaseous components are removed at from 10 mbar to atmospheric pressure.

9. The process as claimed in claim 1, wherein the 3-hydroxyacetanilide used is a 3-hydroxyacetanilide-containing reaction mixture prepared by reacting 3-aminophenol with acetic anhydride in acetic acid.

10. The process as claimed in claim 1, wherein a ratio of from 1.5 to 5 parts by weight of aliphatic carboxylic acid per part by weight of 3-hydroxyacetanilide employed is set.

* * * * *